United States Patent
Reevell

(10) Patent No.: US 11,819,051 B2
(45) Date of Patent: Nov. 21, 2023

(54) ELECTRICALLY OPERATED AEROSOL-GENERATING SYSTEM WITH MEANS TO DETECT A TUBULAR AEROSOL-GENERATING ARTICLE

(71) Applicant: Philip Morris Products S.A., Neuchatel (CH)

(72) Inventor: Tony Reevell, London (GB)

(73) Assignee: Philip Morris Products S.A., Neuchatel (CH)

( * ) Notice: Subject to any disclaimer, the term of this patent is extended or adjusted under 35 U.S.C. 154(b) by 746 days.

(21) Appl. No.: 16/305,143

(22) PCT Filed: May 26, 2017

(86) PCT No.: PCT/EP2017/062789
§ 371 (c)(1),
(2) Date: Nov. 28, 2018

(87) PCT Pub. No.: WO2017/207442
PCT Pub. Date: Dec. 7, 2017

(65) Prior Publication Data
US 2020/0316325 A1    Oct. 8, 2020

(30) Foreign Application Priority Data
May 31, 2016    (EP) .................................... 16172321

(51) Int. Cl.
*A24D 1/20*    (2020.01)
*A24F 40/46*    (2020.01)
(Continued)

(52) U.S. Cl.
CPC ................ *A24D 1/20* (2020.01); *A24F 40/46* (2020.01); *A24F 40/53* (2020.01); *A61M 11/042* (2014.02);
(Continued)

(58) Field of Classification Search
CPC ........ A23F 40/10; A23F 40/485; A23F 40/53; A23F 40/20; A23F 47/00; A23F 47/002;
(Continued)

(56) References Cited

U.S. PATENT DOCUMENTS 5,498,855 A    3/1996 Deevi et al.
5,514,630 A    5/1996 Willkens et al.
(Continued)

FOREIGN PATENT DOCUMENTS

CN    103929988 A    7/2014
CN    104135881 A    11/2014
(Continued)

OTHER PUBLICATIONS

Combined Chinese Office Action and Search Report dated Dec. 28, 2020 in Chinese Patent Application No. 201780028189.7 (with English translation), 15 pages.
(Continued)

*Primary Examiner* — Alex B Efta
(74) *Attorney, Agent, or Firm* — Oblon, McClelland, Maier & Neustadt, L.L.P.

(57) ABSTRACT

An electrically operated aerosol-generating system is provided, including a main unit and a tubular aerosol-generating article. The main unit includes a heating portion disposed at an outer surface of the main unit. The heating portion includes one or more electric heaters. The tubular aerosol-generating article includes a tubular aerosol-forming substrate and an inner passage, wherein the inner passage is configured to receive the heating portion of the main unit. The one or more electric heaters of the heating portion of the main unit are arranged to heat the tubular aerosol-forming substrate when the tubular aerosol-generating article is received on the heating portion of the main unit. The aerosol-generating system further includes means to deter-
(Continued)

mine that the tubular aerosol-generating article is received on the heating portion of the main unit.

19 Claims, 3 Drawing Sheets

(51) Int. Cl.
| | |
|---|---|
| A24F 40/53 | (2020.01) |
| A24F 40/51 | (2020.01) |
| A61M 11/04 | (2006.01) |
| A61M 15/06 | (2006.01) |
| A24B 15/167 | (2020.01) |
| A24F 40/20 | (2020.01) |

(52) U.S. Cl.
CPC ............ *A61M 15/06* (2013.01); *A24B 15/167* (2016.11); *A24F 40/20* (2020.01); *A61M 2205/3368* (2013.01); *A61M 2205/36* (2013.01); *A61M 2205/8206* (2013.01)

(58) Field of Classification Search
CPC ........... A23F 47/0008; A61M 15/0063; A61M 15/0036; A61M 15/06
See application file for complete search history.

(56) References Cited

U.S. PATENT DOCUMENTS

| | | | | |
|---|---|---|---|---|
| 5,665,262 | A | * | 9/1997 | Hajaligol ................. A24F 40/46 131/194 |
| 5,902,501 | A | | 5/1999 | Nunnally et al. |
| 2010/0163063 | A1 | | 7/2010 | Fernando et al. |
| 2011/0126848 | A1 | | 6/2011 | Zuber et al. |
| 2011/0155718 | A1 | | 6/2011 | Greim et al. |
| 2014/0064715 | A1 | | 3/2014 | Greim et al. |
| 2014/0196736 | A1 | | 7/2014 | Fernando et al. |
| 2014/0299137 | A1 | * | 10/2014 | Kieckbusch ............ A24F 40/51 131/328 |
| 2015/0128976 | A1 | * | 5/2015 | Verleur .................... A24F 40/90 131/329 |
| 2015/0272226 | A1 | | 10/2015 | Zuber et al. |
| 2016/0174613 | A1 | | 6/2016 | Zuber et al. |
| 2016/0302488 | A1 | | 10/2016 | Fernando et al. |
| 2016/0374145 | A1 | | 12/2016 | Greim et al. |
| 2016/0374402 | A1 | | 12/2016 | Fernando et al. |
| 2017/0055589 | A1 | | 3/2017 | Fernando et al. |
| 2017/0231278 | A1 | * | 8/2017 | Mironov ................. G01F 23/26 392/390 |
| 2017/0340010 | A1 | * | 11/2017 | Bilat ........................ A24F 40/60 |
| 2017/0347708 | A1 | * | 12/2017 | Shin ........................ A24F 40/40 |
| 2018/0140015 | A1 | * | 5/2018 | Carroll ................... A24F 40/485 |

FOREIGN PATENT DOCUMENTS

| | | |
|---|---|---|
| CN | 104886779 A | 9/2015 |
| CN | 106488714 A | 3/2017 |
| EP | 2 316 286 A1 | 5/2011 |
| EP | 2 327 318 A1 | 6/2011 |
| JP | 2012-513750 A | 6/2012 |
| JP | 2013-509160 A | 3/2013 |
| KR | 10-2011-0096548 A | 8/2011 |
| RU | 2 676 506 C1 | 12/2018 |
| WO | WO 99/20940 A1 | 4/1999 |
| WO | WO 03/095688 A2 | 11/2003 |
| WO | WO 2011/079933 A1 | 7/2011 |
| WO | WO 2015/082560 A1 | 6/2015 |
| WO | WO 2016/005602 A1 | 1/2016 |

OTHER PUBLICATIONS

International Search Report and Written Opinion issued Sep. 13, 2017 in PCT/EP2017/062789, filed May 26, 2017.
Korean Office Action dated Jun. 23, 2022 in Korean Patent Application No. 10-2018-7031865 (with English translation), 13 pages.

* cited by examiner

ELECTRICALLY OPERATED AEROSOL-GENERATING SYSTEM WITH MEANS TO DETECT A TUBULAR AEROSOL-GENERATING ARTICLE

The present invention relates to an electrically operated aerosol-generating system. In particular, the present invention relates to an electrically operated aerosol-generating system comprising a tubular aerosol-generating article and a main unit.

Known handheld electrically operated aerosol-generating systems typically comprise an aerosol-generating device or a main unit comprising a battery, control electronics and an electric heater for heating an aerosol-generating article designed specifically for use with the aerosol-generating device. In some examples, the aerosol-generating article comprises an aerosol-forming substrate, such as a tobacco rod or a tobacco plug. Aerosol-forming substrates, such as tobacco, typically comprise one or more volatile compounds that form an aerosol when heated inside the aerosol-generating device. The heater contained within the aerosol-generating device is inserted into or around the aerosol-forming substrate when the aerosol-generating article is inserted into the aerosol-generating device. In some electrically operated aerosol-generating systems, the aerosol-generating article may comprise a capsule containing an aerosol-forming substrate, such as loose tobacco.

It would be desirable to provide a system that improves the transfer of heat between the electric heaters and the aerosol-generating article. It would be desirable to provide a system that prevents power from being supplied to the electric heaters when the aerosol-generating article is not fully received by the main unit.

In addition, existing systems may enable a main unit to be used with different aerosol-generating articles. The tubular aerosol-generating articles may comprise aerosol-forming substrates having different compositions. Some aerosol-forming substrates may not be suitable for use with some aerosol-generating systems. For example, some aerosol-forming substrates may be damaged or spoiled by high temperatures. A manufacturer of an aerosol-generating system may authorise certain aerosol-forming substrates for use in their aerosol-generating systems. Authorised aerosol-forming substrates may have suitable properties for use in the aerosol-generating system. However, a user may place a tubular aerosol-generating article having an unauthorised and unsuitable aerosol-forming substrate on the main unit. Some unauthorised aerosol-forming substrates may damage the aerosol-generating system. Some unauthorised aerosol-forming substrates may be harmful to a user.

It would be desirable for a system to be able to distinguish between aerosol-generating articles.

According to a first aspect of the present invention, there is provided an electrically operated aerosol-generating system comprising a main unit and a tubular aerosol-generating article. The main unit comprises a heating portion arranged at an outer surface of the main unit. The heating portion comprises one or more electric heaters. The tubular aerosol-generating article comprises a tubular aerosol-forming substrate and an inner passage, wherein the inner passage is configured to receive the heating portion of the main unit. The one or more electric heaters of the heating portion of the main unit are arranged to heat the tubular aerosol-forming substrate when the tubular aerosol-generating article is received on the heating portion of the main unit. The aerosol-generating system further comprises means to determine that the tubular aerosol-generating article is received on the heating portion of the main unit.

As used herein, the term 'aerosol-generating article' is used to describe an article comprising an aerosol-forming substrate that, when heated, releases volatile compounds that can form an aerosol.

As used herein, the term 'main unit' is used to describe a device that interacts with a tubular aerosol-generating article to generate an aerosol. The main unit typically includes a supply of electrical energy and associated electric circuitry to operate the one or more heating elements.

As used herein, the terms 'inner' and 'outer' refer to relative positions of parts of the tubular aerosol-generating article or the main unit.

As used herein, the term 'inner surface' refers to a surface of an article or a main unit that faces towards the interior of the article or main unit. For example, the inner passage of the tubular aerosol-generating article may be defined by an inner surface. Likewise, the term 'outer surface' refers to a surface of an article or a main unit that faces towards the exterior or outwardly from the system. For example, the heating portion of the main unit is arranged at an outer surface of the main unit. As such, the one or more electric heaters are arranged at the outer surface of the main unit and may be visible to a user when a tubular aerosol-generating article is not received on the heating portion of the main unit.

The means to determine that the tubular aerosol-generating article is received on the heating portion of the main unit may enable the aerosol-generating system to inform a user when the tubular aerosol-generating article is received on the heating portion of the main unit. In other words, this may enable the aerosol-generating system to determine when the tubular aerosol-generating article is arranged correctly on the main unit for use.

The means to determine that the tubular aerosol-generating article is received on the heating portion of the main unit may comprise a sensor. Suitable sensors include, for example, light sensors, proximity sensors and pressure sensors.

The sensor may be arranged at any suitable location on the main unit. The sensor may be arranged at or towards the proximal end of the main unit. The sensor may be arranged between the heating portion and the proximal end of the main unit. The sensor may be arranged proximal to the heating portion. The sensor may be arranged at or towards the heating portion of the main unit. The sensor may be arranged at the outer surface of the main unit. The sensor may be arranged at or towards an end of the heating portion. The sensor may be arranged distal to the heating portion. The sensor may be arranged between the heating portion and the distal end of the main unit. Where the main unit comprises a shoulder between the heating portion and a distal portion of the main unit, the sensor may be arranged at the shoulder.

As used herein, the terms 'proximal' and 'distal' are used to describe the relative positions of components or portions of the aerosol-generating system, aerosol-generating article or main unit of the invention. As used herein, the 'proximal' end of the system is the end on which a user may draw on in use in order to inhale an aerosol generated by the aerosol-generating system. The 'proximal' end may also be referred to as the mouth end. The 'distal' end of the aerosol-generating system is the end opposite to the 'proximal' end. The 'distal' end is the end that is furthest from the user in use.

The means to determine that the tubular aerosol-generating article is received on the heating portion of the main unit may further comprise electric circuitry configured to determine that the tubular aerosol-generating article is received on the heating portion of the main unit based on signals received from the sensor.

The main unit may comprise electric circuitry configured to prevent the supply of power to the one or more electric heaters when the means to determine that the tubular aerosol-generating article is received on the heating portion of the main unit determines that the tubular aerosol-generating article is not received on the heating portion of the main unit. This may substantially prevent power from being supplied to the one or more electric heaters when the one or more electric heaters are not fully covered by the tubular aerosol-generating article.

For example, where the tubular aerosol-generating article is opaque, the main unit may comprise means to determine that the tubular aerosol-generating article is received on the heating portion of the main unit in the form of a light sensor. The main unit may comprise a shoulder and the light sensor may be arranged at the shoulder of the main unit. The light sensor may be arranged to be substantially covered or obscured by the distal end of the tubular aerosol-generating article when the tubular aerosol-generating article is received on the heating portion of the main unit. The main unit may further comprise electric circuitry configured to determine that the tubular aerosol-generating article is received on the heating portion of the main unit based on measurements from the light sensor. The electric circuitry may be configured to determine that the tubular aerosol-generating article is received on the heating portion of the main unit when the intensity of light sensed by the light sensor falls below a predetermined threshold value. The predetermined threshold value may correspond to the lowest intensity expected to be sensed by the light sensor when the light sensor is not covered by the tubular aerosol-generating article. The electric circuitry may be configured to inhibit the supply of power to the one or more electric heaters until the electric circuitry determines that the tubular aerosol-generating article is received on the heating portion. When the electric circuitry determines that the tubular aerosol-generating article is received on the heating portion, the electric circuitry may be configured to enable power to be supplied to the one or more electric heaters.

The means to determine that the tubular aerosol-generating article is received on the heating portion of the main unit may comprise: a first electrical contact arranged on the main unit and a second electrical contact arranged on the main unit, spaced from the first electrical contact. The means to determine that the tubular aerosol-generating article is received on the heating portion of the main unit may also comprise electric circuitry configured to sense an electrical connection between the first electrical contact and the second electrical contact and determine that the tubular aerosol-generating device is received on the heating portion of the main unit based on the sensed electrical connection.

The tubular aerosol-generating article may comprise an electrically conductive material. The electrically conductive material may be arranged on the tubular aerosol-generating article to electrically connect the first and second electrical contacts of the main unit when the tubular aerosol-generating article is received on the heating portion of the main unit.

The electrical contacts may be arranged at any suitable position on the main unit. The electrical contacts may be arranged at or towards the proximal end of the main unit. The electrical contacts may be arranged proximal to the heating portion. The electrical contacts may be arranged between the heating portion and the proximal end of the main unit. The electrical contacts may be arranged at or towards the heating portion of the main unit. The electrical contacts may be arranged at the outer surface of the main unit. The electrical contacts may be arranged at or towards an end of the heating portion. The electrical contacts may be arranged distal to the heating portion. The electrical contacts may be arranged between the heating portion and the distal end of the main unit. Where the main unit comprises a shoulder against which the distal end of the tubular aerosol-generating article abuts when the tubular aerosol-generating article is received on the heating portion, the electrical contacts may be arranged at the shoulder.

The electrical contacts may be any suitable shape. The electrical contacts may be elongate. The electrical contacts may comprise one or more elongate strips. The one or more elongate strips may be arranged at the outer surface of the main unit. The one or more elongate strips may extend substantially the length of the heating portion. The electrical contacts may be substantially annular. The electrical contacts may comprise one or more annular rings. The one or more rings may substantially circumscribe a portion of the outer surface of the main unit. Where the main unit comprises a shoulder against which the distal end of the tubular aerosol-generating article abuts when the tubular aerosol-generating article is received on the heating portion the electrical contacts may comprise one or more rings substantially circumscribing a portion of the shoulder. The electrical contacts may be the same shape. The electrical contacts may be different shapes.

The electrical contacts may be spaced in any suitable direction on the main unit. The electrical contacts may be spaced along the length of the main unit. The first electrical contact may be arranged proximal to the second electrical contact. The electrical contacts may be spaced around the circumference of the main unit.

The electrically conductive material may comprise any suitable material. Suitable electrically conductive materials include metals, alloys, electrically conductive ceramics and electrically conductive polymers. As used herein with respect to the present invention, an electrically conductive material refers to a material having a volume resistivity at 20° C. of less than about $1\times10^{-5}$ Ωm, typically between about $1\times10^{-5}$ Ωm and about $1\times10^{-9}$ Ωm. The materials may include gold and platinum. The electrically conductive material may be coated with a passivation layer. The electrically conductive material may comprise or be coated in material that is sufficiently non-reactive so as not to react with or contaminate the tubular aerosol-forming substrate. The electrically conductive material may comprised transparent or translucent material. For example, a suitable transparent material may be Indium Tin Oxide (ITO).

The electrically conductive material may be arranged at any suitable position on the tubular aerosol-generating article. The electrically conductive material may be arranged at or towards an end of the tubular aerosol-generating article. The electrically conductive material may be arranged at an end face of the tubular aerosol-generating article. The electrically conductive material may be arranged at the inner surface of the inner passage of the tubular aerosol-generating article. The electrically conductive material may be arranged at or towards an end of the inner passage. The electrically conductive material may be arranged at or towards the middle of the length of the inner passage. Where the inner passage of the tubular aerosol-generating article comprises two open ends configured to receive the heating portion of the main unit, the electrically conductive material may be arranged at both ends of the tubular aerosol-generating article.

The electrically conductive material may be any suitable shape. The electrically conductive material may be elongate. The electrically conductive material may comprise one or more elongate strips. The one or more elongate strips may be arranged at the inner surface of the inner passage. The one or more elongate strips may extend substantially the length of the inner passage. The electrically conductive material may be substantially annular. The electrically conductive material may comprise one or more annular rings. The one or more rings may substantially circumscribe a portion of the inner surface of the inner passage. The one or more rings may substantially circumscribe a portion of at least one end face of the tubular aerosol-generating article.

The electrical contacts and the electrically conductive material may be shaped and arranged such that the electrically conductive material may electrically connect the spaced electrical contacts when the tubular aerosol-generating article is received on the heating portion of the main unit. For example, where the electrical contacts are annular electrical contacts spaced along the length of the main unit, the electrically conductive material may be an elongate strip extending along the length of the inner passage. In another example, where the main unit comprises a shoulder against which the distal end of the tubular aerosol-generating article abuts when the tubular aerosol-generating article is received on the heating portion, the electrically conductive material comprises one or more rings circumscribing at least one end face of the tubular aerosol-generating article.

Providing at least one of an annular electrically conductive material circumscribing the inner passage or an end face of the tubular aerosol-generating article and annular electrical contacts circumscribing the outer surface of the main unit or a shoulder of the main unit may eliminate the need to maintain a specific rotational orientation of the tubular aerosol-generating article relative to the main unit upon insertion of the main unit into the inner passage of the tubular aerosol-generating article.

The main unit may comprise means to determine the identity of the tubular aerosol-generating article. Identifying the tubular aerosol-generating article may enable the main unit to identify an unsuitable, unauthorised or unknown tubular aerosol-generating article received on the heating portion of the main unit. This may substantially prevent or inhibit use of aerosol-generating articles that may cause damage to the main unit. This may substantially prevent or inhibit use of aerosol-generating articles that are potentially harmful to the user. Identification of the tubular aerosol-generating article received on the heating portion may also enable the aerosol-generating system to distinguish between suitable or authentic aerosol-generating articles. This may enable the aerosol-generating system to be operated in different modes depending on the identity of the tubular aerosol-generating article.

As used herein, the terms "determine the identity" and "identify" are used to describe verification, authentication or recognition of a tubular aerosol-generating article. For example, identifying a tubular aerosol-generating article may include determining at least one of the composition of the tubular aerosol-forming substrate and the origin or authenticity of the tubular aerosol-generating article. Similarly, the term 'identity' is used to describe at least one of the composition of the tubular aerosol-forming substrate, the suitability and the authenticity of the tubular aerosol-generating article.

The tubular aerosol-generating article may comprise an identifier. The tubular aerosol-generating article may be marked with the identifier. Any suitable identifier may be used. For example, the identifier may be a visual identifier, such as a barcode or an alphanumeric code. The identifier may be unique to each particular aerosol-generating article. The identifier may be unique to each type of aerosol-generating article. In another example, the identifier may be the same for aerosol-generating articles comprising aerosol-forming substrates having the same composition.

The identifier may be arranged on the tubular aerosol-generating article at any suitable position. The identifier may be arranged on the inner surface of the inner passage. The identifier may be arranged at any suitable position along the length of the inner passage. The identifier may be arranged at an end face of the tubular aerosol-generating article. Where the tubular aerosol-generating article comprises two open ends configured to receive the heating portion of the main unit, the identifier may be arranged at both open ends.

The means to determine the identity of the tubular aerosol-generating article may be configured to determine the identity of the tubular aerosol-generating article based on the identifier. The means to determine the identity of the tubular aerosol-generating article may comprise means for reading the identifier. The means for reading the identifier may comprise any suitable means for reading the identifier, such as optical scanning, digital photography and image processing, or magnetic scanning. The means for reading the identifier may be an optical scanner. The means for reading the identifier may be arranged on the main unit similarly to the sensors described above in relation to the means for determining when the tubular aerosol-generating article is received on the heating portion of the main unit.

The means for reading the identifier may comprise a sensor. The means to determine the identity of the tubular aerosol-generating article may comprise electric circuitry configured to determine the identity of the tubular aerosol-generating article based on signals received from the sensor. The tubular aerosol-forming substrate may comprise an identifier arranged to be sensed by the sensor when the tubular aerosol-generating article is received on the heating portion of the main unit.

For example, the means to determine the identity of the tubular aerosol-generating article may comprise an optical sensor and electric circuitry configured to determine the identity of the tubular aerosol-generating article based on signals received from the optical sensor. The tubular aerosol-generating article may comprise a visual identifier, such as a barcode, arranged to be sensed by the optical sensor when the tubular aerosol-generating article is received by the heating portion of the main unit.

The means to determine the identity of the tubular aerosol-generating article may comprise: a first electrical contact arranged on the main unit and a second electrical contact arranged on the main unit and spaced from the first electrical contact. The tubular aerosol-generating article may comprise an electrical identifier, such as a strip of electrically conductive material. The electrically conductive material may be arranged on the tubular aerosol-generating article to electrically connect the first and second electrical contacts of the main unit when the tubular aerosol-generating article is received on the heating portion of the main unit. The means to determine the identity of the tubular aerosol-generating article may further comprise electric circuitry configured to sense an electrical quantity between the first electrical contact and the second electrical contact and determine the identity of the tubular aerosol-generating article based on the sensed electrical quantity.

The electrical contacts and the electrically conductive material may be shaped and arranged as described above in relation to means to determine that the tubular aerosol-generating article is received on the heating portion of the main unit. The electrical contacts and the electrically conductive material for the means to determine the identity of the tubular aerosol-generating article may also be the electrical contacts and the electrically conductive material for the means to determine that the tubular aerosol-generating article is received on the heating portion of the main unit.

The main unit may comprise electric circuitry configured to sense an electrical connection between the first and second electrical contacts. The main unit may be configured to determine the identity of the tubular aerosol-generating article based on the sensed electrical connection. In other words, the presence of the electrical connection may indicate that the aerosol-generating article is an authentic aerosol-generating article produced by an authorised manufacturer for the aerosol-generating system.

The main unit may comprise electric circuitry configured to measure an electrical quantity between the first electrical contact and the second electrical contact. The electric circuitry may be configured to determine the identity of the tubular aerosol-generating article based on the measured electrical quantity.

As used herein, the term 'electrical quantity' is used to describe any electrical property, parameter or attribute of a system that can be quantified by measurement. For example, suitable 'electrical quantities' include impedance, capacitance and resistance. The electric circuitry may be configured to measure at least one of impedance, capacitance and resistance.

The electric circuitry may be configured to determine that the tubular aerosol-generating article is received on the heating portion of the main unit and to identify the tubular aerosol-generating article using the same electrical contacts on the main unit and electrically conductive material on the tubular aerosol-generating article.

The main unit may comprise electric circuitry configured to determine whether the tubular aerosol-generating article received on the heating portion is a tubular aerosol-generating article produced or approved by the manufacturer of the aerosol-generating system based on the measured electrical quantity information. In other words, the electric circuitry may be configured to determine whether the tubular aerosol-generating article is authentic.

The electric circuitry may be configured to identify whether the sensed information matches an expected value or range of values for an authentic aerosol-generating article that is suitable for use with the main unit. For example, the electric circuitry may be configured to identify whether measured electrical quantity information matches an expected value or range of values for an authentic aerosol-generating article that is suitable for use with the main unit.

Reference identity information may be stored in a memory of the electric circuitry. The reference aerosol-generating article identity information may be associated with reference measurement information. For example, the reference identity information may be associated with reference electrical quantity information. The electric circuitry may be configured to compare sensed information to the stored reference measurement information. The electric circuitry may be configured to associate the sensed information with stored reference aerosol-generating article identity information based on a match.

The reference information may be information that has been previously measured by the electric circuitry and stored in a memory of the electric circuitry. This may enable the identification of aerosol-generating article received on the heating portion to be reliable for each particular main unit.

The aerosol-generating system of the present invention comprises a tubular aerosol-generating article comprising a tubular aerosol-forming substrate. The tubular configuration of the aerosol-generating article and the aerosol-forming substrate may facilitate improved conductive heat transfer from the one or more electric heaters of the main unit to the aerosol-forming substrate. The tubular aerosol-forming substrate may have a larger surface area to volume ratio than a conventional body or a plug of aerosol-forming substrate of equivalent size, without an inner passage. The tubular shape of the aerosol-forming substrate may reduce the maximum thickness of the aerosol-forming substrate. This may facilitate propagation of heat through the aerosol-forming substrate. This may facilitate aerosol generation.

The tubular aerosol-generating article may be any suitable shape and size. The tubular aerosol-generating article may be substantially cylindrical. The tubular aerosol-generating article may be substantially elongate. The tubular aerosol-generating article may comprise a cylindrical open-ended hollow tube of aerosol-forming substrate. The tubular aerosol-generating article may have any suitable cross-section. For example, the cross-section of the tubular aerosol-generating article may be substantially circular, cylindrical, square or rectangular.

The tubular aerosol-generating article may have a width of between about 5 mm and about 20 mm, between about 5 mm and about 12 mm or about 8 mm.

The tubular aerosol-generating article may have a length of between about 10 mm and about 100 mm, or between about 10 mm and about 50 mm, between about 30 mm and about 60 mm or about 45 mm.

The length of the tubular aerosol-generating article may be substantially similar to the length of the heating portion of the main unit. The length of the tubular aerosol-generating article may be equal to or greater than the length of the heating portion of the main unit such that tubular aerosol-generating article covers the one or more electric heaters when the tubular aerosol-generating article is received on the heating portion of the main unit.

As used herein, the term 'width' is used to describe the maximum dimension in the transverse direction of the aerosol-generating system, the tubular aerosol-generating article and the main unit. When used herein, the term 'length' is used to describe the maximum dimension in the longitudinal direction of the aerosol-generating system, the tubular aerosol-generating article and the main unit.

As used herein, the term 'longitudinal' is used to describe the direction between the proximal or mouth end and the distal end of the aerosol-generating system and the term 'transverse' is used to describe the direction perpendicular to the longitudinal direction.

The tubular aerosol-generating article comprises an inner passage. As used herein, the term 'inner passage' refers to a passage extending through at least part of the article. The inner passage may be surrounded by an annular body and may extend substantially along a longitudinal axis of the article.

The inner passage of the tubular aerosol-generating article may be any suitable shape and may have any suitable cross-section. For example, the cross-section of the inner passage may be substantially circular, cylindrical, square or rectangular.

The inner passage may be arranged substantially centrally in the tubular aerosol-generating article. As such, the thickness of the tubular aerosol-forming substrate may be substantially consistent around the circumference of the tubular aerosol-generating article. This may enable even heating of the tubular aerosol-forming substrate about the circumference of the tubular aerosol-generating article.

The inner passage may have a width of between about 2 mm and about 18 mm, between about 2 mm and about 10 mm or about 4 mm.

The width of the inner passage of the tubular aerosol-generating article may be substantially similar to the width of the heating portion of the main unit. As such, the inner surface of the inner passage may contact or abut the outer surface of the heating portion of the main unit when the tubular aerosol-generating article is received on the heating portion. The width of the inner passage of the tubular aerosol-generating article may be smaller than the width of the heating portion of the main unit, such that the tubular aerosol-generating article is received on the heating portion with a friction or an interference fit.

The tubular aerosol-forming substrate may be a solid aerosol-forming substrate. The tubular aerosol-forming substrate may be a solid aerosol-forming substrate at room temperature. The tubular aerosol-forming substrate may comprise a tobacco-containing material containing volatile tobacco flavour compounds which are released from the substrate upon heating. The tubular aerosol-forming substrate may comprise a non-tobacco material. The tubular aerosol-forming substrate may comprise tobacco-containing material and non-tobacco containing material.

The solid aerosol-forming substrate may comprise, for example, one or more of: powder, granules, pellets, shreds, strands, strips or sheets containing one or more of: herb leaf, tobacco leaf, tobacco ribs, expanded tobacco and homogenised tobacco.

The solid aerosol-forming substrate may contain tobacco or non-tobacco volatile flavour compounds, which are released upon heating of the solid aerosol-forming substrate. The solid aerosol-forming substrate may also contain one or more capsules that, for example, include additional tobacco volatile flavour compounds or non-tobacco volatile flavour compounds and such capsules may melt during heating of the solid aerosol-forming substrate.

The solid aerosol-forming substrate may be provided on or embedded in a thermally stable carrier. The carrier may take the form of powder, granules, pellets, shreds, strands, strips or sheets. The solid aerosol-forming substrate may be deposited on the surface of the carrier in the form of, for example, a sheet, foam, gel or slurry. The solid aerosol-forming substrate may be deposited on the entire surface of the carrier. The solid aerosol-forming substrate may be deposited in a pattern to provide a non-uniform flavour delivery during use.

The tubular aerosol-forming substrate may comprise a gathered textured sheet of homogenised tobacco material. The tubular aerosol-forming substrate may comprise a gathered textured sheet of homogenised tobacco material comprising one or more of a plurality of spaced-apart indentations, protrusions and perforations. Use of a textured sheet of homogenised tobacco material may facilitate gathering of the sheet of homogenised tobacco material to form the tubular aerosol-forming substrate.

As used herein, the term 'sheet' refers to a laminar element having a width and length substantially greater than a thickness. As used herein, the term 'gathered' is used to describe a sheet that is convoluted, folded, or otherwise compressed or constricted substantially transversely to a longitudinal axis of the tubular aerosol-generating article. As used herein, the term 'textured sheet' denotes a sheet that has been crimped, embossed, debossed, perforated or otherwise deformed. As used herein, the term 'homogenised tobacco material' refers to a material formed by agglomerating particulate tobacco.

The tubular aerosol-forming substrate may comprises a gathered crimped sheet of homogenised tobacco material. As used herein, the term 'crimped sheet' refers to a sheet having a plurality of substantially parallel ridges or corrugations. Preferably, the substantially parallel ridges or corrugations extend along or parallel to a longitudinal axis of the tubular aerosol-generating article. This may facilitate gathering of the crimped sheet of homogenised tobacco material to form the tubular aerosol-generating article. However, it will be appreciated that crimped sheets of homogenised tobacco material for inclusion in the tubular aerosol-generating article may alternatively or in addition have a plurality of substantially parallel ridges or corrugations that are disposed at an acute or obtuse angle to the longitudinal axis of the tubular aerosol-generating article.

The tubular aerosol-forming substrate may comprise one or more aerosol formers. The tubular aerosol-forming substrate may comprise a single aerosol former. The tubular aerosol-forming substrate may comprise two or more aerosol formers. The tubular aerosol-forming substrate may have an aerosol former content of greater than about 5 percent on a dry weight basis. The aerosol aerosol-forming substrate may have an aerosol former content of between about 5 percent and approximately 30 percent on a dry weight basis. The tubular aerosol-forming substrate may have an aerosol former content of about 20 percent on a dry weight basis.

As used herein, the term 'aerosol former' refers to any suitable known compound or mixture of compounds that, in use, facilitates formation of an aerosol and that is substantially resistant to thermal degradation at the operating temperature of the tubular aerosol-generating article. Suitable aerosol-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate.

The tubular aerosol-generating article may comprise one or more layers circumscribing the tubular aerosol-forming substrate. For example, the tubular aerosol-generating article may comprise one or more wrappers wrapped around the tubular aerosol-forming substrate.

The one or more layers may comprise a thermally insulating material. Wrapping a layer of thermally insulating material around the tubular aerosol-forming substrate may facilitate retention of heat from the one or more electric in the tubular aerosol-generating article. This may improve the conductive heat-transfer efficiency of the aerosol-generating system. As used herein the term 'thermally insulating material' is used to describe material having a bulk thermal conductivity of less than about 50 milliwatts per metre Kelvin (mW/(m·K)) at 23° C. and a relative humidity of 50% as measured using the modified transient plane source (MTPS) method. The thermally insulating material may also have a bulk thermal diffusivity of less than or equal to about 0.01 square centimetres per second (cm2/s) as measured using the laser flash method.

The one or more layers may comprise a material that is substantially impermeable to gases, such as air. Circumscribing the tubular aerosol-forming substrate with a layer of material that is substantially impermeable to gas may facilitate retention of vapour generated by the tubular aerosol-generating article in the aerosol-generating system and may facilitate direction of the vapour towards the user.

The one or more layers may comprise any suitable material. The one or more layers may comprise a paper-like material. The one or more layers may comprise cigarette paper. The one or more layers may comprise tipping paper.

The inner passage of the tubular aerosol-forming substrate may be the inner passage of the tubular aerosol-generating article. As such, the one or more electric heaters of the main unit may be adjacent to or in contact with the tubular aerosol-forming substrate when the tubular aerosol-generating article is received on the heating portion of the main unit. However, in some embodiments, the tubular aerosol-generating article may comprise one or more layers circumscribing the inner surface of the inner passage of the tubular aerosol-forming substrate. The one or more inner layers may comprise substantially the same material as described above in relation to the one or more outer layers.

At least one end of the inner passage of the tubular aerosol-generating article may be open and configured to receive the heating portion of the main unit. The inner passage of the tubular aerosol-generating article may comprises two open ends configured to receive the heating portion of the main unit.

The tubular aerosol-generating article may comprise additional components.

The tubular aerosol-generating article may comprise a mouthpiece. The mouthpiece may be arranged at the proximal end of the tubular aerosol-generating article. Where the tubular aerosol-generating article comprises a mouthpiece, the tubular aerosol-generating article may comprise a proximal end comprising the mouthpiece and a distal end comprising an open end of the inner passage configured to receive the heating portion of the main unit.

The mouthpiece may be a single segment or component mouthpiece. The mouthpiece may be a multi-segment or multi-component mouthpiece. The mouthpiece may comprise a material of low or very low filtration efficiency. The mouthpiece may comprise a filter comprising one or more segments comprising any suitable filtration materials. Suitable filtration materials are known in the art and include, but are not limited to, cellulose acetate and paper. The mouthpiece may comprise one or more segments comprising absorbents, adsorbents, flavourants, and other aerosol modifiers and additives or combinations thereof. The mouthpiece may have a width that is substantially equal to the width of the tubular aerosol-generating article.

Where the tubular aerosol-generating article comprises a mouthpiece, the tubular aerosol-generating article may be configured such that the main unit terminates inside the tubular aerosol-generating article. The proximal end of the main unit may abut or contact the mouthpiece when the tubular aerosol-generating article is received on the heating portion of the main unit. The proximal end of the main unit may be spaced from the mouthpiece when the tubular aerosol-generating article is received on the heating portion of the main unit.

The tubular aerosol-generating article may comprise additional components, including at least one of an aerosol-cooling element and a transfer element arranged between the tubular aerosol-forming substrate and the mouthpiece.

The tubular aerosol-generating article may comprise a cooling element arranged between the tubular aerosol-forming substrate and the mouthpiece. The cooling element may comprise a plurality of longitudinally extending channels. The cooling element may comprise a gathered sheet of material selected from the group consisting of metallic foil, polymeric material, and substantially non-porous paper or cardboard.

The tubular aerosol-generating article may comprise a transfer element or spacer element arranged between the tubular aerosol-forming substrate and the mouthpiece. The transfer element may facilitate cooling of the aerosol generated by the heated the tubular aerosol-forming substrate. The transfer element may also facilitate adjustment of the length of the aerosol-generating system to a desired value, for example to a length similar to that of a conventional cigarette. The transfer element may comprise at least one open-ended tubular hollow body formed from one or more suitable materials that are substantially thermally stable at the temperature of the aerosol generated by the transfer of heat from the combustible heat source to the aerosol-forming substrate. Suitable materials are known in the art and include, but are not limited to, paper, cardboard, plastics, such a cellulose acetate, ceramics and combinations thereof.

Where the tubular aerosol-generating article comprises one or more layers or wrappers circumscribing the tubular aerosol-forming substrate, the one or more layers or wrappers may also circumscribe any of the additional components, such as the mouthpiece, the cooling element and the transfer element.

According to a second aspect of the present invention, there is provided a tubular aerosol-generating article for an electrically operated aerosol-generating system according to the first aspect of the present invention. The tubular aerosol-generating article comprises: a tubular aerosol-forming substrate; and an inner passage configured to receive a heating portion of a main unit of an electrically operated aerosol-generating system and an identifier.

The aerosol-generating system of the present invention also comprises a main unit. The main unit may comprise a housing. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. The material may be light and non-brittle. The main unit may comprise a proximal portion and a distal portion. The proximal portion and the distal portion of the main unit may have different shapes and dimensions.

The proximal portion of the main unit may comprise the heating portion. As used herein, the term 'heating portion' is used to describe the portion of the main unit that comprises the one or more electric heaters. The extent of the heating portion is determined by the extent of the heaters along the length of the main unit.

The heating portion may have any suitable shape and dimensions. The shape and dimensions of the heating portion may be substantially similar to the shape and dimensions of the inner passage of the tubular aerosol-generating article. The shape and dimensions of the heating portion may be complimentary to the shape of the inner passage of the tubular aerosol-generating article.

The heating portion may be substantially cylindrical. The heating portion may be substantially elongate. The heating portion may have any suitable cross-section. For example, the cross-section of the heating portion may be substantially circular, elliptical, square or rectangular. The shape of the heating portion may be substantially similar to the shape of the inner passage of the tubular aerosol-generating article. The shape of the heating portion may be complimentary to the shape of the inner passage of the tubular aerosol-generating article.

Where the cross-sections of the heating portion and the tubular aerosol-generating article are not circularly symmetrical, the tubular aerosol-generating article may be received on the heating portion at specific rotational orientations. Where the cross-sections of the heating portion and the tubular aerosol-generating article are circularly symmetrical, this may eliminate the need to maintain a specific rotational orientation of the tubular aerosol-generating article for the tubular aerosol-generating article to be received by the heating portion.

The heating portion may have a width of between about 2 mm and about 18 mm, between about 2 mm and about 10 mm or about 4 mm. The heating portion may have a length of between about 10 mm and about 100 mm, or between about 10 mm and about 50 mm or about 45 mm.

The main unit may comprise any suitable number of electric heaters. The main unit may comprise one electric heater. The main unit may comprise two or more electric heaters. The main unit may comprise two, three, four, five, six, seven eight or nine electric heaters. Where the main unit comprises two or more electric heaters, the two or more electric heaters may be spaced around the circumference of the heating portion. The two or more electric heaters may be spaced along the length of the heating portion. Where the heating portion comprises three or more electric heaters, the three or more electric heaters may be spaced evenly across the heating portion. The three or more electric heaters may be spaced unevenly across the heating portion.

The one or more electric heaters may be any suitable shape. The one or more electric heaters may be elongate. The one or more electric heaters may extend substantially the length of the heating portion. The one or more electric heaters may be substantially annular. The one or more electric heaters may comprise one or more annular rings. The one or more rings may substantially circumscribe a portion of the outer surface of the main unit. The one or more rings may substantially circumscribe a portion of the proximal end of the heating portion. The one or more rings may substantially circumscribe a portion of the distal end of the heating portion.

The one or more electric heaters may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Examples of suitable composite heater elements are disclosed in U.S. Pat. No. 5,498,855, WO-A-03/095688 and U.S. Pat. No. 5,514,630.

The distal portion of the main unit may be any suitable shape and dimensions.

The distal portion may be substantially cylindrical. The distal portion may be substantially elongate. The distal portion may have any suitable cross-section. For example, the cross-section of the distal portion may be substantially circular, elliptical, square or rectangular. The distal portion may be configured to be held by a user during use of the aerosol-generating system.

The width of the distal portion of the main unit may be larger than the width of the proximal portion of the main unit. This may provide a larger space in the distal portion than in the proximal portion and may enable the distal portion to accommodate a power supply and electric circuitry.

The width of the distal portion of the main unit may be similar to the width of the tubular aerosol-generating article. As such, when the tubular aerosol-generating article is received on the heating portion of the main unit, the aerosol-generating system may form a substantially cylindrical unit having a substantially consistent width along its length. This may enable the aerosol-generating system to resemble a conventional smoking article, such as a cigar or a cigarette.

The distal portion may have a width of between about 5 mm and about 20 mm, between about 5 mm and about 12 mm or about 8 mm. The distal portion may have a length of between about 10 mm and about 100 mm, or between about 10 mm and about 50 mm or about 45 mm.

The main unit may comprise a shoulder between the heating portion and the distal portion of the main unit. The shoulder may connect the outer surface of the proximal portion of the main unit to the outer surface of the distal portion of the main unit. The shoulder may comprise an angled, sloped or bevelled surface joining the proximal portion of the main unit and the distal portion of the main unit. The shoulder may comprise a wall extending substantially radially outwards from the outer surface of the proximal portion of the main unit to the outer surface of the distal portion of the main unit.

The proximal portion of the main unit may be configured such that the distal end of the tubular aerosol-generating article may abut or contact the shoulder when the tubular aerosol-generating article is received on the heating portion. As such, the shoulder may act as a stop to inhibit movement of the tubular aerosol-generating article beyond the heating portion in a distal direction relative to the main unit. This may facilitate positioning of the tubular aerosol-generating article on the heating portion of the main unit in the desired position along the length of the main unit.

The main unit may further comprise a distal stop. The distal stop may be arranged distal to the heating portion of the main unit. The distal stop may be configured to engage with the distal end of the tubular aerosol-generating article when the tubular aerosol-generating article is received on the heating portion. Where the main unit comprises a shoulder between the proximal portion and the distal portion, there distal stop may be arranged between the heating portion and the shoulder.

The main unit may comprise one or more electric power supplies. The one or more electric power supplies may be arranged in the distal portion of the main unit. The one or more power supplies may comprise a battery. The battery may be a Lithium based battery, for example a Lithium-Cobalt, a Lithium-Iron-Phosphate, a Lithium Titanate or a Lithium-Polymer battery. The battery may be a Nickel-metal hydride battery or a Nickel cadmium battery. The one or more power supplies may comprise other forms of charge storage devices, such as capacitors. The one or more power supplies may require recharging and may be configured for many cycles of charge and discharge. The one or more power supplies may have a capacity that allows for the storage of enough energy for one or more user experiences; for example, the one or more power supplies may have sufficient capacity to allow for the continuous generation of aerosol for a period of around six minutes, corresponding to the typical time taken to smoke a conventional cigarette, or for a period that is a multiple of six minutes. In another example, the one or more power supplies may have sufficient capacity to allow for a predetermined number of puffs or discrete activations of the heating means and actuator.

The main unit may comprise electric circuitry configured to control the supply of power to the one or more electric heaters from the one or more electrical power supplies. Where the main unit comprises two or more electric heaters, the electric circuitry may be configured to supply power to all of the electric heaters simultaneously. Where the main unit comprises two or more electric heaters, the electric circuitry may be configured to supply power to each electric heater separately. The electric circuitry may be configured to supply power to each electric heater selectively. The electric circuitry may be configured to supply power to the electric heaters sequentially. The electric circuitry may be configured to supply power to selected ones of the electric heaters in a predetermined sequence. For example, the electric circuitry may be configured to supply power to one heater per puff. In another example, the electric circuitry may be configured to supply power to a first heater for a predetermined period of time and subsequently to supply power to a second heater for a predetermined period of time. This may enable selective heating of portions of the aerosol-forming substrate. This may enable variation of the aerosol supplied to the user during a puff. This may enable portions of the aerosol-forming substrate to be heated to different temperatures. This may enable the aerosol-generating system to preserve unheated portions of aerosol-forming substrate for each puff of a user experience.

The main may comprise a user input, such as a switch or button. This may enable the user to switch the main unit on and off. The switch or button may activate the aerosol-generating means. The switch or button may initiate aerosol generation. The switch or button may prepare the electric circuitry to await input from the puff detector.

The electric circuitry may comprise a sensor or a puff detector to detect air flow through the aerosol-generating system indicative of a user taking a puff. The electric circuitry may be configured to provide supply power to the one or more electric heaters when the sensor senses a user taking a puff.

The main unit may comprise a mouthpiece. The mouthpiece may be arranged at the proximal end of the main unit. The mouthpiece may be configured to allow a user to suck, puff or draw on the mouthpiece to draw air and vapour through one or more airflow pathways of the aerosol-generating system.

The mouthpiece may comprise retaining means in accordance with the present invention. For example, the mouthpiece may comprise one or more of the one or more protrusions. In another example, the mouthpiece may comprise the second magnetic material.

The mouthpiece may be removably receivable on the main unit. Where the mouthpiece is removable from the main unit, the mouthpiece may comprise a cover arranged to overlap the tubular aerosol-generating article when the tubular aerosol-generating article is received on the heating portion of the main unit. The cover may further facilitate retention of heat around the tubular aerosol-generating article and may inhibit the exit of vapour from the tubular aerosol-generating article through the outer surface of the tubular aerosol-generating article.

According to a third aspect of the present invention, there is provided a main unit for an electrically operated aerosol-generating system according to the first aspect of the present invention. The main unit comprises a heating portion arranged at an outer surface of the main unit. The heating portion comprises one or more electric heaters and means to determine that a tubular aerosol-generating article is received on the heating portion of the main unit.

The main unit may have a proximal portion and a distal portion, the heating portion of the main unit being arranged at the proximal portion of the main unit. The means to determine that the tubular aerosol-generating article is received on the heating portion of the main unit may be arranged between the heating portion and the distal portion of the main unit.

The main unit may also comprise means to determine the identity of a tubular aerosol-generating article when a tubular aerosol-generating article is received on the heating portion of the main unit.

When the electrically operated aerosol-generating system is assembled for use and the tubular aerosol-generating article is received on the heating portion of the main unit, the aerosol-generating system may have a substantially cylindrical shape. The aerosol-generating system may have a total length of between about 70 mm and about 200 mm, or between about 70 mm and about 150 mm, or about 120 mm. The aerosol-generating system may have a width of between about 5 mm and about 20 mm, between about 5 mm and about 10 mm or about 8 mm.

The main unit may be configured to be durable. The main unit may be configured to be reusable.

The tubular aerosol-generating article may be configured to be a disposable component. The tubular aerosol-generating article may be configured to be disposed after a single user experience. In contrast, the main unit may be configured to be durable and reusable. The main unit may comprise relatively expensive and durable components of the aerosol-generating system, such as a power supply, heaters, and electric circuitry.

The tubular aerosol-generating article may be manufactured, stored and sold separately from the main unit. Each tubular aerosol-generating article may be individually packaged. A plurality of the tubular aerosol-generating articles may be packaged and sold together, similarly to conventional smoking articles such as cigarettes.

The aerosol-generating system may be an electrically operated smoking system. The overall dimensions of the aerosol-generating system may be similar to a conventional smoking article such as a cigarette, a cigar a cigarillo or any other such smoking article.

Embodiments in accordance with the present invention will now be described in detail, by way of example only, with reference to the accompanying drawings, in which.

Figure 1:
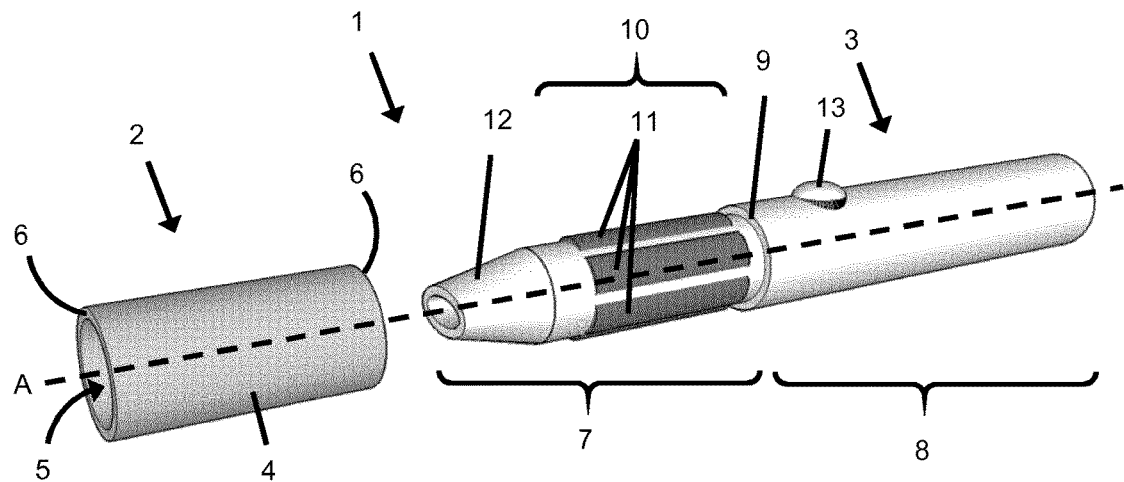
FIG. 1 is a schematic illustration of an electrically operated aerosol-generating system comprising a main unit and a tubular aerosol-generating article.
Figure 2:
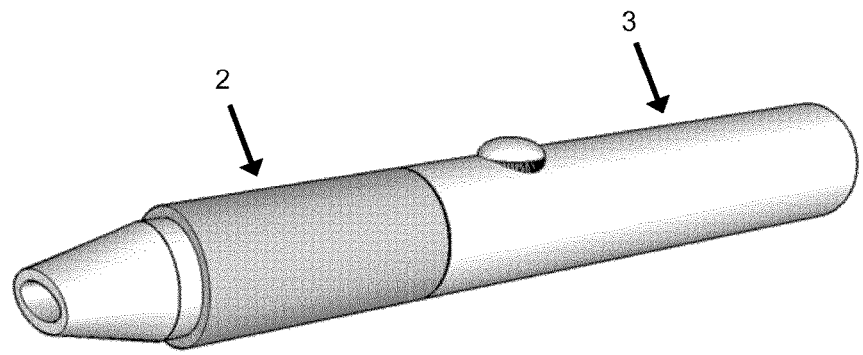
FIG. 2 is a schematic illustration of the electrically operated aerosol-generating system of FIG. 1, showing the tubular aerosol-generating article fully received on the main unit.
Figure 3:
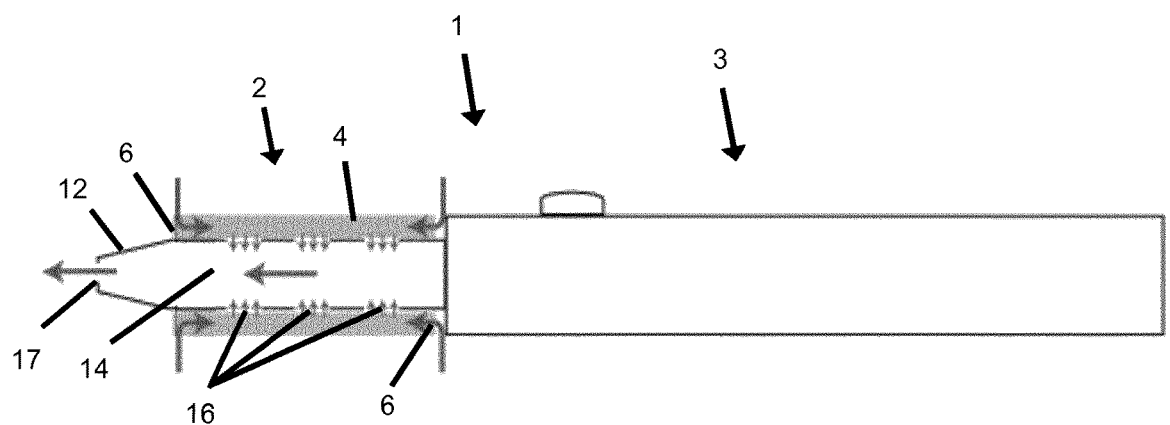
FIG. 3 is a schematic illustration of the electrically operated aerosol-generating system of FIG. 1 showing airflow through the aerosol-generating system when the aerosol-generating article is fully received on the main unit and a user is drawing on the mouthpiece.

An exemplary electrically operated aerosol-generating system having a tubular aerosol-generating article is shown in FIGS. 1 to 3. The electrically operated aerosol-generating system 1 comprises a tubular aerosol-generating article 2 and a main unit 3.

The tubular aerosol-generating article 2 comprises a cylindrical open-ended hollow tube of aerosol-forming substrate 4. An inner passage 5 extends centrally through the tubular aerosol-forming substrate 4 and extends the length of the tubular aerosol-forming substrate 4 such that both ends of the inner passage 5 are open. Both open ends of the inner passage 5 are configured to receive a proximal portion 7 of the main unit 3.

The tubular body of aerosol-forming substrate 4 comprises one or more gathered sheets of tobacco circumscribed by an outer wrapper (not shown), which covers the cylindrical outer surface of the tubular body of aerosol-forming substrate 4. The outer wrapper is formed of a material that is substantially impermeable to gas, such that the outer wrapper substantially prevents ambient air from being drawn into the tubular aerosol-generating article 2 through the cylindrical outer surface. The outer wrapper also substantially prevent vapour from the heated aerosol-forming substrate 4 from leaving the tubular aerosol-generating article 2 via the cylindrical outer surface.

The outer wrapper does not extend over the annular end faces 6 of the tubular aerosol-forming substrate 4, such that the annular end faces 6 of the tubular aerosol-forming substrate 4 are exposed to ambient air. Ambient air may be drawn into the tubular aerosol-generating article 2 through either annular end face 6. Similarly, the open ends of the inner passage 5 are not covered by the outer wrapper, such that the proximal portion 7 of the main unit 3 may be inserted into either end of the inner passage 5.

The main unit 3 comprises a substantially circularly-cylindrical hollow housing formed of a rigid, thermally insulating material, such as PEEK. The main unit 3 comprises a proximal portion 7 and a distal portion 8 that are separated by a shoulder 9.

The proximal portion 7 comprises a heating portion 10 having seven identical electrical heaters 11. The seven electric heaters 11 are spaced evenly around the circumference of the heating portion 10. Each of the electrical heaters 11 is elongate and arranged with its length extending in the direction along a longitudinal axis A of the main unit 3. The length of each electric heater 11 is substantially similar to the length of the tubular aerosol-generating article 2. As such, when the tubular aerosol-generating article 2 is received on the heating portion 10 of the main unit 3, the tubular aerosol-generating article 2 overlaps and covers the electrical heaters 11 along their entire length. This enables a substantial proportion of the heat produced by the heaters 11 to be transferred to the aerosol-forming-substrate 4 rather than to ambient air during use of the aerosol-generating system.

The heating portion 10 of the main unit 3 has a circularly-cylindrical cross-section that is substantially similar to the cross-section of the inner passage 5 of the tubular aerosol-generating article 2. The width of the heating portion 10 is slightly larger than the width of the inner passage 5. As such, the heating portion 10 of the main unit 3 may be inserted into the inner passage 5 of the tubular aerosol-generating article with an interference or a friction fit. The interference or friction fit ensures contact between the electric heaters 11 at the outer surface of the heating portion 10 of the main unit 3 and the inner surface of the inner passage 5 of the tubular aerosol-generating article 2, when the tubular aerosol-generating article 2 is received on the heating portion 10. This contact facilitates heat transfer between the heaters 11 and the tubular aerosol-forming substrate 4. The interference of friction fit also provides some resistance against movement of the tubular aerosol-generating article 2 along the longitudinal axis A of the main unit 3. As such, the interference or friction fit helps to retain the tubular aerosol-generating article 2 on the heating portion 10 of the main unit 3.

The proximal portion 7 of the main unit 3 further comprises a tapered mouthpiece 12 at the proximal end of the main unit 3 for a user to draw upon to receive aerosol generating by the aerosol-generating system.

The distal portion 8 of the main unit 3 has a cylindrical cross-section that is substantially similar to the cylindrical cross-section of the tubular aerosol-generating article 2. The width of the distal portion 8 is substantially similar to the width of the tubular aerosol-generating article 2. As such, when the tubular aerosol-generating article 2 is received on the heating portion 10 of the main unit 3, the electrically operated aerosol-generating system 1 forms a substantially circularly-cylindrical unit having a consistent width or diameter that may resemble a conventional cigarette or cigar, as shown in FIG. 2.

The distal portion 8 of the main unit 2 houses a battery (not shown) and electric circuitry (not shown) inside the hollow housing. The battery is arranged and configured to supply power to the electric heaters 11 of the heating portion 10. The electric circuitry is configured to control the supply of power from the battery to the electric heaters 11. The electric circuitry comprises a sensor for detecting a user's puff on the mouthpiece 12.

The electric circuitry is configured to supply power to the electric heaters 11 either simultaneously or individually in a predetermined sequence. In other words, the electric circuitry is configured to supply power to the electric heaters 11 in different heating modes, such as a simultaneous heating mode and a sequential heating mode. For example, in a simultaneous heating mode, the electric circuitry is configured to supply power to all of the heaters 11 when a puff is detected. In another example, in a sequential mode, the electric circuitry is configured to supply electrical power to a first one of the heaters 11 when a first puff is detected, to supply electrical power a second one of the heaters 11 when a second puff is detected and to subsequently supply power to individual ones of the remaining heaters 11, in sequence, for each detected puff until all of the heaters have been activated.

A push button 13 is also provided on the distal portion 8 of the main unit 3. The electric circuitry is configured to switch between heating modes on depression of the push button 13. Consecutive depressions of the push button 13 switch the heating mode of the electric circuitry between a sequential heating mode, a simultaneous heating mode and a no power mode (off).

The width of the distal portion 8 of the main unit 3 is larger than the width of the proximal portion 7. As such, the main unit 3 comprises a shoulder 9 separating the proximal portion 7 from the distal portion 8. The shoulder 9 comprises a wall extending substantially radially outwardly from the distal end of the proximal portion 7 to the proximal end of the distal portion 8.

A distal stop (not shown) is arranged on the proximal portion 7 of the main unit 3, between the heating portion 10 and the shoulder 9. The distal stop is configured to engage with the distal end of the tubular aerosol-generating article 2 when the tubular aerosol-generating article 2 is fully received on the heating portion 10. The distal stop substantially prevents movement of the tubular aerosol-generating article 2 beyond the heating portion 10 in a distal direction towards the distal portion 8.

It will be appreciated that in some embodiments, the shoulder 9 may act as the distal stop for the tubular aerosol-generating article 2. In these embodiments, the shoulder 9 may abut or contact the distal end of the tubular aerosol-generating article 2 when the tubular aerosol-generating article 2 is fully received on the heating portion 10.

As shown in FIG. 3, an air passage 14 extends through the proximal portion 7 of the main unit 3. A plurality of air inlets 16 are arranged in the outer face of the heating portion 10, between the electric heaters 11, and an air outlet 17 is provided in the mouthpiece 12. The plurality of air inlets 16 and the air outlet 17 are fluidly connected to the air passage 14 to enable air to be drawn through the air passage 14 when a user draws on the mouthpiece 12.

To assemble the electrically operated aerosol-generating system 1 for use, a user aligns main unit 3 and the inner passage of the tubular aerosol-generating article 2 along a common longitudinal axis A, with either end of the tubular aerosol-generating article 2 facing the proximal end of the main unit 3. The user moves the tubular aerosol-generating article 2 along the common axis A towards the main unit 3, such that the proximal end of the main unit 3 is inserted into the distal open end of the inner passage 5. The user slides the tubular aerosol-generating article 2 over the proximal portion 7 of the main unit 3, towards the distal portion 8, until the distal end of the tubular aerosol-generating article 2 abuts the distal stop (not shown). In this position, the tubular aerosol-generating article 2 is fully received on the heating portion 10 of the main unit 3, and the tubular aerosol-generating article 2 covers the electric heaters 11 and the air inlets 16, as shown in FIGS. 2 and 3.

In use, the user depresses the push button 13 to switch the main unit 3 from the off mode into the sequential heating mode. The user draws on the mouthpiece 12 of the main unit 3, and the electric circuitry (not shown) detects the user's puff on the mouthpiece 12. On detection of the user's puff, the electric circuitry supplies power from the power supply (not shown) to one of the electric heaters 11. The powered electric heater 11 heats a portion of the tubular aerosol-forming substrate 4 of the tubular aerosol-generating article 2. As the portion of the aerosol-forming substrate 4 is heated, volatile compounds of the aerosol-forming substrate vapourise and generating a vapour.

When the user draws on the mouthpiece 12 of the main unit 3, ambient air is drawn into the tubular aerosol-generating article 2 through the annular end faces 6 of the tubular aerosol-forming substrate 4. The air drawn into the tubular aerosol-generating article 2 is drawn through the tubular aerosol-forming substrate 4 towards the air inlets 16 of the main unit 3. The vapour generated by the heated aerosol-forming substrate is entrained in the air is drawn through the aerosol-forming substrate 4. The entrained vapour is drawn out of the tubular aerosol-forming substrate 4 at the inner face of the inner passage 5 and enters the air passage 14 of the main unit 3 through the air inlets 16. The entrained vapour is drawn through the air passage 14 in a proximal direction towards the mouthpiece 12. As the vapour is drawn through the air passage 14, the vapour cools and forms an aerosol. The aerosol is drawn out of the air passage 14 through the air outlet 17 in the mouthpiece 12, and is delivered to the user for inhalation. The direction of airflow through the system 1 is indicated by the arrows shown in FIG. 3.

It will be appreciated that in some examples the tubular aerosol-generating article may comprise one or more air inlets at the cylindrical outer face, in the form of one or more perforations in the outer layers or wrappers circumscribing the tubular aerosol-forming substrate. In these embodiments, air may be drawn into the tubular aerosol-generating article through the perforations in the cylindrical outer face. The main unit may also comprise additional air inlets arranged distal or proximal to the heating portion. These additional air inlets may not be covered by the tubular aerosol-generating article when the tubular aerosol-generating article is fully received on the heating portion of the main unit. As such, these additional air inlets may enable ambient air to be drawn directly into the air passage of the main unit and may help to cool the vapour and aerosol before inhalation by the user. This may improve the experience for the user.

Figure 4:
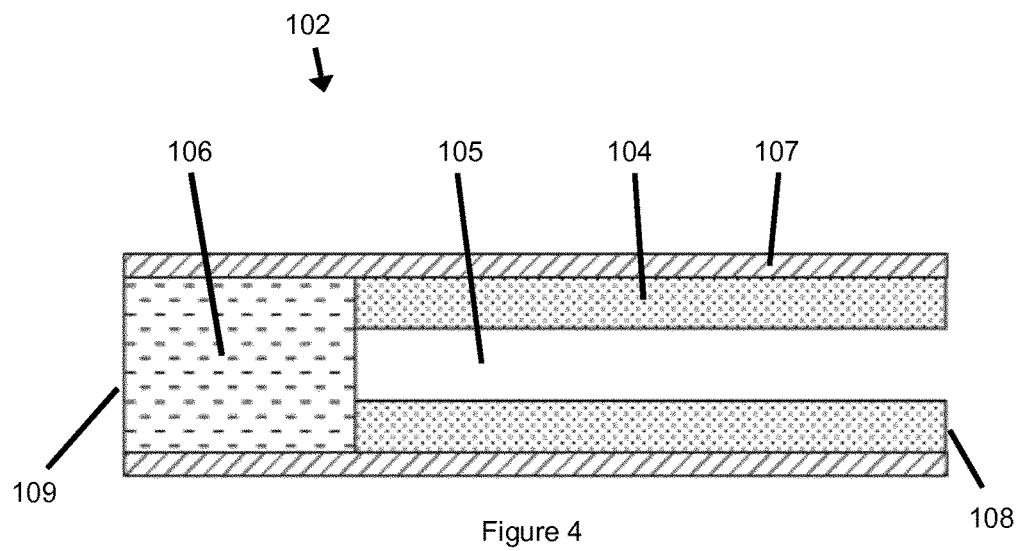
FIG. 4 is a schematic illustration of another example of a tubular aerosol-generating article.
Figure 5:
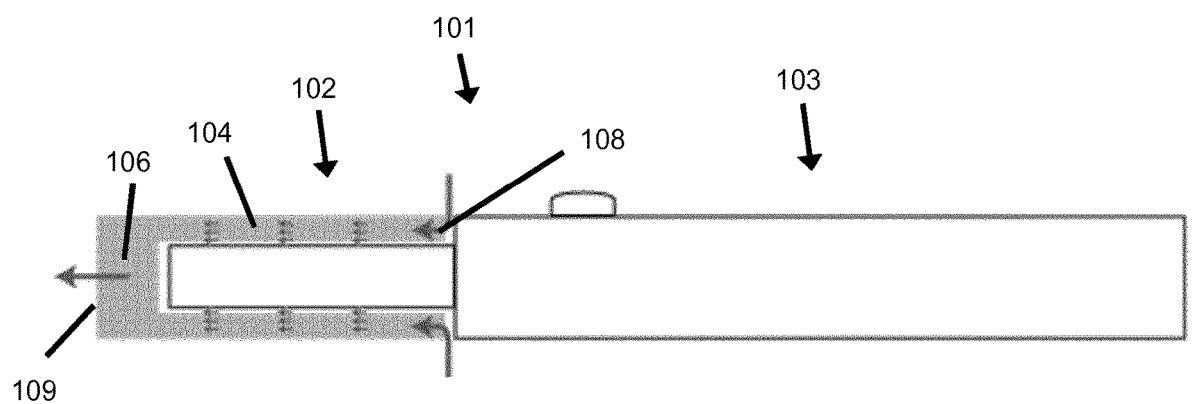
FIG. 5 is a schematic illustration of the tubular aerosol-generating article of FIG. 4 showing airflow through the tubular aerosol-generating article when the tubular aerosol-generating article is fully received on a main unit and a user is drawing on the mouthpiece.

Another example of an electrically operated aerosol-generating system having a tubular aerosol-generating article is shown in FIGS. 4 and 5. The electrically operated aerosol-generating system 101 shown in FIGS. 4 and 5 comprises a tubular aerosol-generating article 102 and a main unit 103.

The tubular aerosol-generating article 102 comprises a cylindrical open-ended hollow tube of aerosol-forming substrate 104. An inner passage 105 extends centrally through the tubular aerosol-forming substrate 104 and extends the length of the tubular aerosol-forming substrate 104 such that both ends of the inner passage 105 are open.

The tubular aerosol-generating article 102 further comprises a mouthpiece 106. The mouthpiece 106 comprises a circularly-cylindrical body of cellulose acetate, having a substantially similar circular cross-section and width to the tubular aerosol-forming substrate 104. The tubular aerosol-forming substrate 104 and the mouthpiece 106 are arranged in abutting coaxial alignment, such that the tubular aerosol-forming substrate 104 and mouthpiece 106 are configured to form a rod. The proximal end of the tubular aerosol-forming substrate 104 abuts the distal end of a mouthpiece 106.

The tubular aerosol-forming substrate 104 and the mouthpiece 106 are circumscribed by an outer wrapper 107. The outer wrapper 107 secures the tubular aerosol-forming substrate 104 to the mouthpiece 106. The outer wrapper 107 is formed of a material that is substantially impermeable to gas, such that the outer wrapper 107 substantially prevents ambient air from being drawn into the tubular aerosol-generating article 102 through the cylindrical outer surface. The outer wrapper 107 covers the cylindrical outer surfaces of the tubular aerosol-forming substrate 104 and the mouthpiece 106, but does not extend over the end faces, such that air may be drawn through the tubular aerosol-generating article 102, from the distal end face 108 to the proximal end face 109.

The distal end of the inner passage 105 is open and is configured to receive a proximal portion of the main unit 103. The proximal end of the inner passage 105 is arranged at the distal end of the mouthpiece 106.

It will be appreciated that the tubular aerosol-generating article 102 may further comprise additional components between the tubular aerosol-forming substrate and the mouthpiece 106.

The main unit 103 is substantially similar to the main unit 3 described above in relation to the example shown in FIGS. 1 to 3. However, The main unit 103 does not comprise an air passage though the proximal portion. As a result, the main unit 103 does not form part of the airflow pathways through the aerosol-generating system 101. In other words, the main unit 103 is substantially isolated from the air drawn through the aerosol-generating system 101.

In addition, the main unit 103 does not comprise a mouthpiece. The heaters (not shown) of the main unit 103 extend to the proximal end of the main unit 103, such that is the proximal end of the main unit is the proximal end of the heating portion.

Since the main unit is substantially isolated from the air drawn through the aerosol-generating system 101, the electric circuitry does not comprise a sensor for detecting a user's puff. In this example, the electric circuitry determines when power is to be supplied to the electric heaters by activation of the push button by the user.

The main unit 103 comprises a distal stop (not shown) arranged between the distal end of the heating portion and the shoulder of the main unit 103. However, it will be appreciated that the distal stop may not be required as the proximal end of the main unit may abut the distal end of the mouthpiece 106 when the tubular aerosol-generating article 102 is fully received on the heating portion.

To assemble the electrically operated aerosol-generating system 101 for use, a user aligns the main unit 103 and the inner passage 105 of the tubular aerosol-generating article 102 along a common longitudinal axis, with the distal end 108 of the tubular aerosol-generating article 102 facing the proximal end of the main unit 103. The user moves the tubular aerosol-generating article 102 along the common axis towards the main unit 103, such that the proximal end of the main unit 103 is inserted into the open distal end of the inner passage 105. The user slides the tubular aerosol-generating article 102 over the proximal portion of the main unit 103, in a distal direction towards the distal portion, until the distal end 108 of the tubular aerosol-generating article 102 abuts the distal stop and the proximal end of the main unit 103 abuts the distal end of the mouthpiece 106. In this position, the tubular aerosol-generating article 102 is fully received on the heating portion of the main unit 103, and the tubular aerosol-generating article 102 covers the electric heaters, as shown in FIG. 5.

In use, the user depresses the push button to switch the main unit 103 from the off mode into the sequential heating mode and the electric circuitry supplies power from the power supply (not shown) to one of the electric heaters. The powered electric heater heats a portion of the tubular aerosol-forming substrate 104 of the tubular aerosol-generating article 102. As the portion of the aerosol-forming substrate 104 is heated, volatile compounds of the aerosol-forming substrate vapourise and generating a vapour.

When the user draws on the mouthpiece 106 of the tubular aerosol-generating article 102, ambient air is drawn into the tubular aerosol-generating article 102 through the distal end face 108 of the tubular aerosol-forming substrate 104. The air drawn into the tubular aerosol-generating article 102 is drawn through the tubular aerosol-forming substrate 104 in a proximal direction towards the mouthpiece 106. The vapour generated by the heated aerosol-forming substrate 104 is entrained in the air being drawn through the aerosol-forming substrate 104. The entrained vapour is drawn out of the tubular aerosol-forming substrate 104 at the proximal end, and enters the mouthpiece 106. The entrained vapour is drawn through the mouthpiece 106 towards the proximal end 109. As the vapour is drawn through the mouthpiece 106, the vapour cools and forms an aerosol. The aerosol is drawn out of the mouthpiece 106 at the proximal end 109, and is delivered to the user for inhalation. The direction of airflow through the system 101 is indicated by the arrows shown in FIG. 5.

It will be appreciated that tubular aerosol-generating articles comprising a mouthpiece, such as the tubular aerosol-generating article 102, may also be used with main units comprising air passages, such as the main unit 3 described above in relation to the example shown in FIGS. 1 to 3. In such systems, the main unit may not comprise a mouthpiece, but rather may comprise an air outlet that is in fluid communication with the mouthpiece of the tubular aerosol-generating article when the tubular aerosol-generating article is fully received on the heating portion of the main unit.

Figure 6:
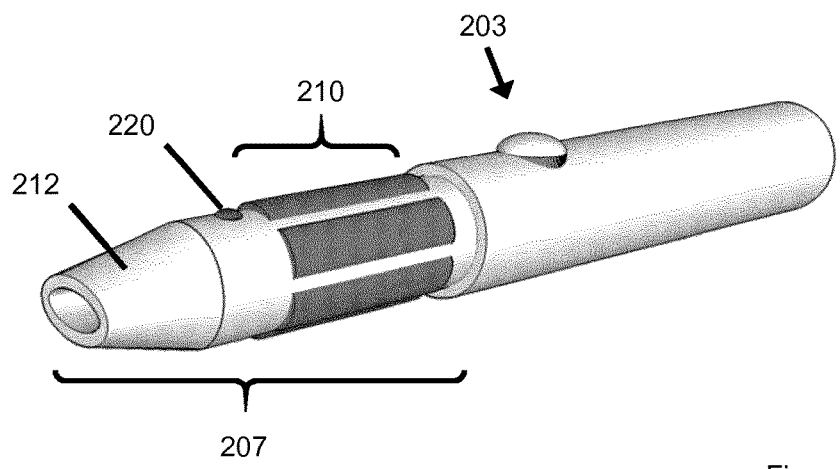
FIG. 6 is a schematic illustration of a main unit for an electrically operated aerosol-generating system according to a first embodiment of the present invention.
Figure 7:
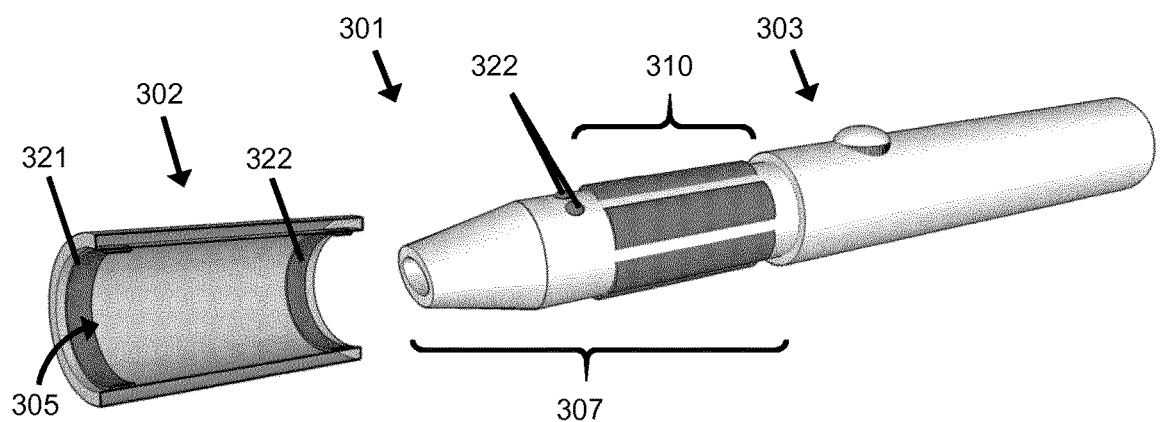
FIG. 7 is a schematic illustration of an electrically operated aerosol-generating system according to a second embodiment of the present invention.
Figure 8:
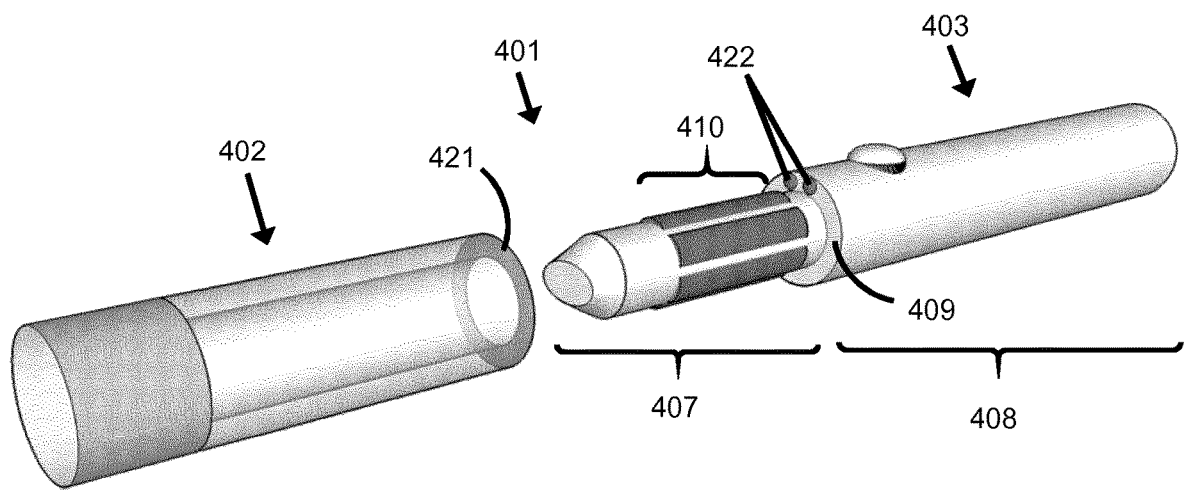
FIG. 8 is a schematic illustration of an electrically operated aerosol-generating system according to a third embodiment of the present invention.

Electrically operated aerosol-generating systems according to several embodiments of the present invention are shown in FIGS. 6 to 8.

FIG. 6 shows a main unit 203 for an electrically operated aerosol-generating system according to a first embodiment of the present invention. The main unit 203 is substantially similar to the main unit 3 described above in relation to FIGS. 1 to 3, and where the same features are present like reference numerals have been used to refer to these features.

The main unit 203 comprises means to determine that a tubular aerosol-generating article is received on the heating portion of the main unit comprising a light sensor 220. The light sensor 220 is arranged on the outer surface of the proximal portion 207, between the heating portion 210 and the mouthpiece 212. At this position, the light sensor is covered by the inner surface of the inner passage of a tubular aerosol-generating article when a tubular aerosol-generating article is received on the heating portion 210 of the main unit 203.

The means to determine that a tubular aerosol-generating article is received on the heating portion of the main unit 203 further comprises electric circuitry (not shown) in the main unit 203 that is configured to determine that a tubular aerosol-generating article is received on the heating portion 210 based on signals received from the light sensor 220. The electric circuitry is configured to determine that a tubular-aerosol-generating article is received on the heating portion 210 of the main unit 203 when the intensity of the light sensed by the light sensor 220 falls below a threshold intensity. A predetermined threshold intensity value is stored in a memory (not shown) of the electric circuitry and compared to measurements of intensity received from the light sensor 220. When the light sensor 220 senses a low light intensity, this indicates that the light sensor 220 is being covered by a tubular aerosol-generating article. When the electric circuitry determines that the sensed light intensity is below the threshold intensity value, the electric circuitry determines that a tubular aerosol-generating article is received on the heating portion 210 of the main unit 203.

It will be appreciated that the light sensor may be arranged at any suitable location on the main unit. For example, the light sensor may be arranged in the heating portion of the main unit or between the heating portion and the distal portion of the main unit. It may be advantageous to arrange the light sensor distal to the heating portion or on the shoulder of the main unit, because in this arrangement the light sensor will only sense a reduction in the intensity of the light when the distal end of the tubular aerosol-generating article is at the distal end of the heating portion, which is the position at which the tubular aerosol-generating article is fully received on the heating portion.

It will also be appreciated that the light sensor may be any other suitable type of sensor, such as a pressure sensor or a proximity sensor.

FIG. 7 shows an electrically operated aerosol-generating system 301 according to a second embodiment of the present invention. The electrically operated aerosol-generating system 301 comprises a tubular aerosol-generating article 302 and a main unit 303. The tubular aerosol-generating article 302 and the main unit 303 are substantially similar to the tubular aerosol-generating article 2 and the main unit 3 described above in relation to FIGS. 1 to 3, and where the same features are present like reference numerals have been used to refer to these features.

The tubular aerosol-generating article 302 comprises two rings 321, 322 comprised of an electrically conductive material, such as aluminium foil. The two rings 321, 322 circumscribe a portion of the inner surface of the inner passage 305. The first ring 321 is arranged at one end of the inner passage 305, and the second ring 322 is arranged at the opposite end of the inner passage 305.

The main unit 303 comprises two electrical contacts 322 arranged on the outer surface of the proximal portion 207, between the heating portion 310 and the mouthpiece 312. A first one of the electrical contacts 322 is spaced about the circumference of the main unit 303 from the second one of the electrical contacts 322. The electrical contacts 322 are arranged such that when the tubular aerosol-generating article 302 is fully received on the heating portion 310 of the main unit, either the first ring 321 abuts or contacts both the first and second electrical contacts 322 or the second ring 322 abuts or contacts both the first and second electrical contacts 322. As such, when the tubular aerosol-generating article 302 is received on the heating portion 310, the first and second electrical contacts 322 are electrically connected by either the first ring 321 or the second ring 322.

The main unit 303 comprises electric circuitry (not shown) configured to monitor for an electrical connection between the first and second electrical contacts 322. The electric circuitry is configured to determine whether a tubular aerosol-generating article is received on the heating portion 310 based on the electrical connection between the first and second electrical contacts 322. If the electric circuitry detects an electrical connection between the first and second electrical contacts 322, the electric circuitry determines that the tubular aerosol-generating article 302 is fully received on the heating portion 310.

The electric circuitry is further configured to prevent electrical power from being supplied from the power supply (not shown) in the main unit 303 to the one or more electrical heaters of the main unit 303 unless an electrical connection is detected between the first and second contacts 322. This means that the electrically operated aerosol-generating system 301 is configured to operate only if the electric circuitry detects that the tubular aerosol-generating article 303 is fully received on the heating portion of the main unit 303.

FIG. 8 shows an electrically operated aerosol-generating system 401 according to a third embodiment of the present invention. The electrically operated aerosol-generating system 401 comprises a tubular aerosol-generating article 402 and a main unit 403. The tubular aerosol-generating article 402 and the main unit 403 are substantially similar to the tubular aerosol-generating article 102 and the main unit 103 described above in relation to FIGS. 4 and 5, and where the same features are present like reference numerals have been used to refer to these features.

The tubular aerosol-generating article 402 comprises a ring 421 of electrically conductive material, such as aluminium, arranged on the distal annular face.

The main unit 403 comprises two electrical contacts 422 arranged on the shoulder 409 between the proximal portion 407 and the distal portion 408. A first one of the electrical contacts 422 is spaced about the circumference of the main unit 403 from the second one of the electrical contacts 422. The first and second electrical contacts 422 are arranged such that when the tubular aerosol-generating article 402 is fully received on the heating portion 410 of the main unit 403, the ring 421 of electrically conductive material abuts or contacts both the first and second electrical contacts 422. As such, when the tubular aerosol-generating article 402 is fully received on the heating portion 410 the first and second electrical contacts 422 are electrically connected by the ring 421.

The electric circuitry of the main unit 403 is configured to determine that the tubular aerosol-generating article 402 is received on the heating portion 410 of the main unit 403 substantially as described above in relation to FIG. 7.

The electric circuitry of the main unit 403 is further configured to determine the identity of the tubular aerosol-forming article 402. The electric circuitry is configured to sense the resistance between the first and second electrical contacts 422. The electric circuitry is configured to determine the identity of the tubular aerosol-generating article 402 based on the sensed resistance between the first and second electrical contacts 422.

The electric circuitry comprises a memory (not shown) storing a lookup table. The lookup table comprises reference resistance information and stored identity information. The stored identity information is associated with the reference resistance information. The electric circuitry is configured to compare the sensed resistance information from the first and second electrical contacts 422 to the stored reference information in the lookup table. If the electric circuitry determines a match between the measured resistance and the stored resistance information, the electric circuitry determines the identity of the tubular aerosol-generating article by determining the stored identity information associated with the matched reference information.

The electric circuitry is also configured to determine a mode of operation of the electric heaters based on the determined identity of the tubular aerosol-generating article. In other words, the electric circuitry is configured to control the power supplied to the one or more electric heaters based on the determined identity of the tubular aerosol-generating article.

Tubular aerosol-generating articles may be provided with different electrically conductive materials, having different resistances, depending on the composition of the tubular aerosol-forming substrate. This enables the main unit to identify each tubular aerosol-generating articles and its associated aerosol-forming substrate composition based on the resistance of the electrically conductive material. This enables the main unit to heat tubular aerosol-generating articles to different temperature depending on the composition of the aerosol-forming substrate. This enables the main unit to be used with different types of tubular aerosol-generating articles having different compositions of aerosol-forming substrate.

The main unit also comprises a display (not shown). The electric circuitry is configured to send the stored identity information associated to the matched reference resistance information to the display to inform the user of the identity of the tubular aerosol-forming substrate received on the heating portion.

It will be appreciated that the electrically conductive material and the electrical contacts may be arranged in any suitable, complimentary arrangement.

It will be appreciated that the examples described herein are straightforward examples, and that modifications may be made to the illustrated circuits to provide different or more sophisticated functionality. It will be appreciated that features described herein with reference to one embodiment may be applied to other embodiments without departing from the scope of the invention.

The invention claimed is:

1. An electrically operated aerosol-generating system, comprising:
   a main unit comprising a heating portion disposed at an outer surface of the main unit, the heating portion comprising one or more electric heaters; and
   a tubular aerosol-generating article comprising:
      a tubular aerosol-forming substrate, and
      an inner passage, wherein:
   the inner passage of the tubular aerosol-generating article is configured to receive the heating portion of the main unit,
   the one or more electric heaters are arranged to heat the tubular aerosol-forming substrate when the tubular aerosol-generating article is received on the heating portion of the main unit,
   the main unit further comprises:
      means to determine that the tubular aerosol-generating article is received on the heating portion of the main unit,
      a proximal portion,
      a distal portion opposite the proximal portion, and
      means to determine an identity of the tubular aerosol-generating article, the proximal portion comprises the heating portion,
   the means to determine that the tubular aerosol-generating article is received on the heating portion of the main unit comprises a sensor,
   the sensor is distal to the heating portion,
   the means to determine the identity of the tubular aerosol-generating article comprises an optical sensor and electric circuitry configured to determine the identity of the tubular aerosol-generating article based on signals received from the optical sensor,
   the tubular aerosol-generating article further comprises a visual indicator, and
   the visual indicator is configured to be sensed by the optical sensor when the tubular aerosol-generating article is received on the heating portion of the main unit.

2. The electrically operated aerosol-generating system according to claim 1, wherein the electric circuitry is configured to prevent power being supplied to the one or more electric heaters when the means to determine that the tubular aerosol-generating article is received on the heating portion of the main unit determines that the tubular aerosol-generating article is not received on the heating portion of the main unit.

3. The electrically operated aerosol-generating system according to claim 1, wherein the electric circuitry is configured to determine that the tubular aerosol-generating article is received on the heating portion of the main unit based on signals received from the sensor.

4. The electrically operated aerosol-generating system according to claim 1, wherein the sensor is selected from the group consisting of: light sensors, proximity sensors, and pressure sensors.

5. The electrically operated aerosol-generating system according to claim 1, wherein
   the tubular aerosol-generating article further comprises an identifier, and
   the means to determine the identity of the tubular aerosol-generating article is configured to determine the identity of the tubular aerosol-generating article based on the identifier.

6. The electrically operated aerosol-generating system according to claim 1, wherein
   a distal end comprising an open end of the inner passage is configured to receive the heating portion of the main unit; and
   the visual indicator is arranged on a face of the open end of the inner passage.

7. A main unit for an aerosol-generating system, the main unit comprising:
   a heating portion disposed at an outer surface of the main unit, the heating portion comprising one or more electric heaters;
   means to determine that a tubular aerosol-generating article is received on the heating portion of the main unit;
   a proximal portion;
   a distal portion opposite the proximal portion; and
   means to determine an identity of the tubular aerosol-generating article, wherein:
   the proximal portion comprises the heating portion,
   the means to determine that the tubular aerosol-generating article is received on the heating portion comprises a sensor,
   the sensor is distal to the heating portion,
   the means to determine the identity of the tubular aerosol-generating article comprises an optical sensor and electric circuitry configured to determine the identity of the tubular aerosol-generating article based on signals received from the optical sensor,
   the tubular aerosol-generating article further comprises a visual indicator, and
   the visual indicator is configured to be sensed by the optical sensor when the tubular aerosol-generating article is received on the heating portion of the main unit.

8. The main unit according to claim 7, wherein the means to determine that the tubular aerosol-generating article is received on the heating portion of the main unit is disposed between the heating portion and the distal portion of the main unit.

9. An electrically operated aerosol-generating system, comprising:
- a main unit comprising a heating portion disposed at an outer surface of the main unit, the heating portion comprising one or more electric heaters; and
- a tubular aerosol-generating article comprising:
  - a tubular aerosol-forming substrate, and
  - an inner passage, wherein:
- the inner passage of the tubular aerosol-generating article is configured to receive the heating portion of the main unit,
- the one or more electric heaters are arranged to heat the tubular aerosol-forming substrate when the tubular aerosol-generating article is received on the heating portion of the main unit,
- the main unit further comprises:
  - means to determine that the tubular aerosol-generating article is received on the heating portion of the main unit,
  - a proximal portion,
  - a distal portion opposite the proximal portion, and
  - means to determine an identity of the tubular aerosol-generating article,
- the proximal portion comprises the heating portion,
- the means to determine that the tubular aerosol-generating article is received on the heating portion of the main unit comprises a sensor,
- the sensor is distal to the heating portion, and
- the means to determine that the tubular aerosol-generating article is received on the heating portion of the main unit further comprises the means to determine the identity of the tubular aerosol-generating article.

10. The electrically operated aerosol-generating system according to claim 9, wherein the main unit further comprises electric circuitry configured to prevent power being supplied to the one or more electric heaters when the means to determine that the tubular aerosol-generating article is received on the heating portion of the main unit determines that the tubular aerosol-generating article is not received on the heating portion of the main unit.

11. The electrically operated aerosol-generating system according to claim 9, wherein the means to determine that the tubular aerosol-generating article is received on the heating portion of the main unit comprises electric circuitry configured to determine that the tubular aerosol-generating article is received on the heating portion of the main unit based on signals received from the sensor.

12. The electrically operated aerosol-generating system according to claim 9, wherein the sensor is selected from the group consisting of: light sensors, proximity sensors, and pressure sensors.

13. The electrically operated aerosol-generating system according to claim 9, wherein
- the tubular aerosol-generating article further comprises an identifier, and
- the means to determine the identity of the tubular aerosol-generating article is configured to determine the identity of the tubular aerosol-generating article based on the identifier.

14. The electrically operated aerosol-generating system according to claim 9, wherein:
- the means to determine the identity of the tubular aerosol-generating article comprises:
  - a first electrical contact disposed on the main unit,
  - a second electrical contact disposed on the main unit and spaced from the first electrical contact, and
  - electric circuitry configured to sense an electrical quantity between the first electrical contact and the second electrical contact and determine the identity of the tubular aerosol-generating article based on the sensed electrical quantity; and
- the tubular aerosol-generating article further comprises an electrical identifier configured to electrically connect the first and the second electrical contacts of the main unit when the tubular aerosol-generating article is received on the heating portion of the main unit.

15. The electrically operated aerosol-generating system according to claim 14, wherein the electrical quantity is a resistance between the first electrical contact and the second electrical contact.

16. The electrically operated aerosol-generating system according to claim 9, wherein
- a distal end comprising an open end of the inner passage is configured to receive the heating portion of the main unit; and
- an identifier arranged on a face of the open end of the inner passage.

17. A main unit for an aerosol-generating system, the main unit comprising:
- a heating portion disposed at an outer surface of the main unit, the heating portion comprising one or more electric heaters;
- means to determine that a tubular aerosol-generating article is received on the heating portion of the main unit;
- a proximal portion;
- a distal portion opposite the proximal portion; and
- means to determine an identity of the tubular aerosol-generating article, wherein:
- the proximal portion comprises the heating portion,
- the means to determine that the tubular aerosol-generating article is received on the heating portion comprises a sensor,
- the sensor is distal to the heating portion, and
- the means to determine that the tubular aerosol-generating article is received on the heating portion of the main unit further comprises the means to determine the identity of the tubular aerosol-generating article.

18. The main unit according to claim 17, wherein the means to determine that the tubular aerosol-generating article is received on the heating portion of the main unit is disposed between the heating portion and the distal portion of the main unit.

19. An electrically operated aerosol-generating system, comprising:
- a main unit comprising a heating portion disposed at an outer surface of the main unit, the heating portion comprising one or more electric heaters; and
- a tubular aerosol-generating article comprising:
  - a tubular aerosol-forming substrate, and
  - an inner passage, wherein:
- the inner passage of the tubular aerosol-generating article is configured to receive the heating portion of the main unit, the one or more electric heaters are arranged to heat the tubular aerosol-forming substrate when the tubular aerosol-generating article is received on the heating portion of the main unit, the main unit further comprises:
- means to determine that the tubular aerosol-generating article is received on the heating portion of the main unit,
- a proximal portion, and
- a distal portion opposite the proximal portion, the proximal portion comprises the heating portion, the means to determine that the tubular aerosol-generating article is received on the heating portion of the main unit comprises a sensor, the sensor is distal to the heating portion, the means to determine that the tubular aerosol-generating article is received on the heating portion of the main unit comprises:
- a first electrical contact disposed on the main unit,
- a second electrical contact disposed on the main unit and spaced from the first electrical contact, and
- electric circuitry configured to sense an electrical connection between the first electrical contact and the second electrical contact and to determine that the tubular aerosol-generating article is received on the heating portion of the main unit based on the sensed electrical connection, and the tubular aerosol-generating article further comprises an electrically conductive material configured to electrically connect the first and the second electrical contacts of the main unit when the tubular aerosol-generating article is received on the heating portion of the main unit.

* * * * *